United States Patent [19]

Schindler et al.

[11] 4,184,935

[45] Jan. 22, 1980

[54] REFERENCE ELECTRODE

[75] Inventors: Johannes G. Schindler; Werner Riemann, both of Marburg, Fed. Rep. of Germany

[73] Assignee: Dr. E. Fresenius Chemisch Pharmazeutische Industrie, Fed. Rep. of Germany

[21] Appl. No.: 803,637

[22] Filed: Jun. 6, 1977

Related U.S. Application Data

[62] Division of Ser. No. 652,349, Jan. 26, 1976, Pat. No. 4,135,999.

[30] Foreign Application Priority Data

Jan. 27, 1975 [DE] Fed. Rep. of Germany ....... 2503176

[51] Int. Cl.$^2$ ............................................. G01N 27/30
[52] U.S. Cl. ............................. 204/195 F; 204/195 M
[58] Field of Search ........... 204/195 R, 195 F, 195 M

[56] References Cited

U.S. PATENT DOCUMENTS

| | | | |
|---|---|---|---|
| 2,927,887 | 3/1960 | Proctor | 204/195 F |
| 3,000,804 | 9/1961 | Cahoon et al. | 204/195 F |
| 3,208,927 | 9/1965 | Arthur et al. | 204/195 F |
| 3,298,944 | 1/1967 | Luck | 204/195 F |
| 3,445,368 | 5/1969 | Detemple | 204/195 F |
| 3,505,196 | 4/1970 | Dahms | 204/195 F |
| 3,741,884 | 6/1973 | Deushane et al. | 204/195 F |
| 3,756,936 | 9/1973 | Neuwelt | 204/195 F |
| 3,843,506 | 10/1974 | Jerrold-Jones | 204/195 F |
| 4,002,547 | 1/1977 | Neti | 204/195 F |

OTHER PUBLICATIONS

Ives et al. "Reference Electrodes", 1961, pp. 467–469, Academic Press, New York & London.

*Primary Examiner*—T. Tung
*Attorney, Agent, or Firm*—Omri M. Behr

[57] ABSTRACT

An ion sensitive electrode comprises a small disc of ion selective polymer for contact with a measuring liquid, the ion selective polymer disc being in contact with a wire of low drift potential relative to the ion selective polymer disc. The invention also includes an electro mechanical measuring arrangement in which the ion sensitive electrode may be used and also a reference electrode suitable for use therewith.

6 Claims, 4 Drawing Figures

REFERENCE ELECTRODE

This is a division of application Ser. No. 652,349, filed Jan. 26, 1976, now U.S. Pat. No. 4,135,999.

BACKGROUND OF THE INVENTION

The invention relates to an ion selective electrode in which an ion selective polymer layer is in contact on the one hand with the measuring liquid and on the other hand with a wire with low drift potential relative to the polymer layer.

Recently, ion selective electrodes have gained considerable importance for electrochemical measurement of various types, particularly in physiology (cf. K. Cammann, "Das Arbeiten mit ionenselektiven Elektroden", Springer-Verlag, Berlin, Heidelberg, New York, 1973). Solid membrane electrodes and liquid membrane electrodes are distinguished from one another. The wire-clad electrodes may be regarded as a further development of the latter (cf. K. Cammann, page 106). They consist of a thin platinum wire which is coated with a layer of polyvinylchloride (PVC). The PVC layer is saturated with the active phase, i.e. the ion selective substance. These electrodes are manufactured with an inner electrolyte in a simple manner in comparison with the normal liquid membrane electrodes, and are also layer or position independent. The selectivity ratio is more favourable than in corresponding liquid membrane electrode types, the pick-up time is very short and the life span is considerably higher than in normal liquid membrane electrodes.

SUMMARY OF THE INVENTION

It is an object of the invention to further improve such electrodes with respect to their reproductbility, the possibility of miniaturizing them, and their versatility of application.

It is a further object of the invention to provide a reference electrode suitable for use with the ion selective electrode of the invention in which the reference electrode is re-shaped so that a stable diffusion potential can be achieved despite a very small contact area.

It is yet a further object of the invention to provide a single rod measuring cell with an ion sensitive electrode and a reference electrode, suitably electrodes in accordance with the invention, which can be used with simple means both for flow measurement and stationary measurement.

According to a first aspect of the invention, there is provided an ion selective electrode comprising a small disc of ion selective polymer for contact with a measuring liquid, a wire with a low drift potential relative to said ion selective polymer disc and a face of said wire in contact with said ion selective polymer disc.

According to a second aspect of the invention, there is provided a reference electrode for use with an ion selective electrode comprising a contact making electrolyte and a small PTFE plate defining an opening as contact area and so small that said contact making electrolyte can flow out of said opening, at normal pressure and room temperature at a rate less than $5 \times 10^{-6}$ μl/sec.

According to a third aspect of the invention, there is provided a single rod measuring cell comprising an electrode body, a reference electrode at one surface of said electrode body, a measuring electrode at the same surface of said electrode body as said reference electrode but spaced a small distance therefrom, a bowl shaped measuring chamber delimited by said one surface of said electrode body and inflow and outflow channels leading into narrow sides of said measuring chamber.

BRIEF DESCRIPTION OF THE DRAWINGS

The invention will now be described in greater detail, by way of example, with reference to the drawings, in which.

DESCRIPTION OF THE PREFERRED EMBODIMENTS

Figure 1:
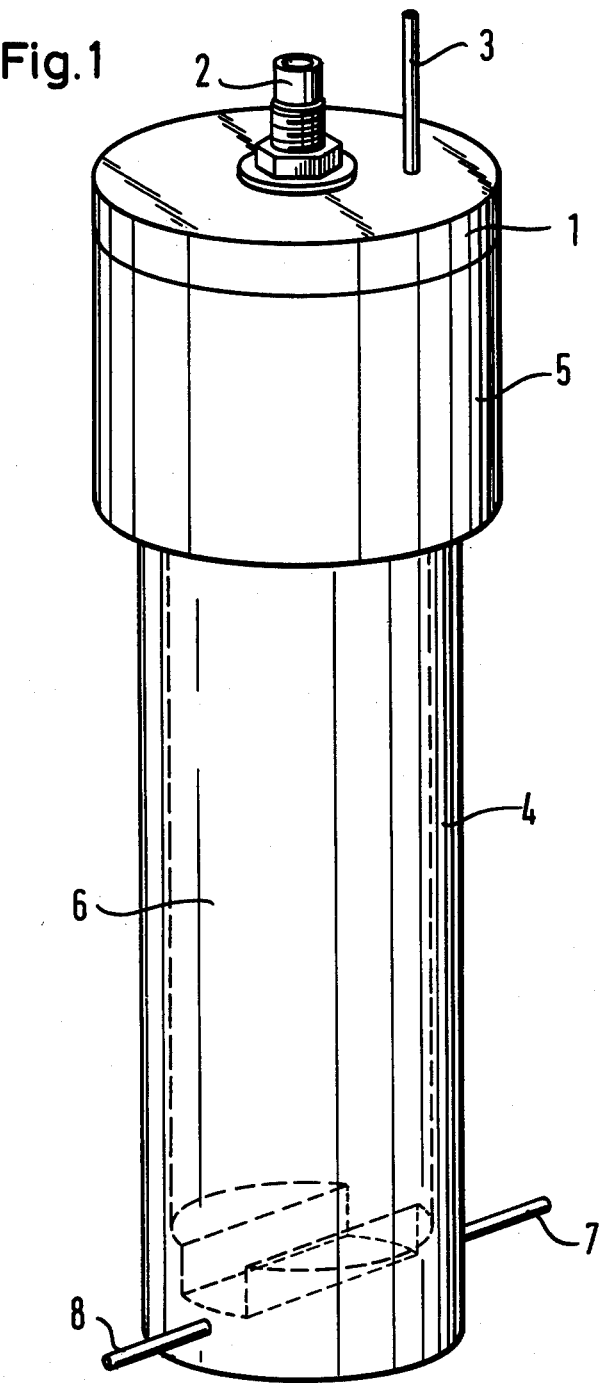
FIG. 1 shows a perspective view of a single-rod measuring cell with the new electrodes.

Basically, the invention proposes that the polymer layer of an ion selective electrode is constructed as a small disc abutting the surface of the wire.

The wire surface to be coated with the selective substance is therefore diminished at the free surface of the wire—preferably a platinum wire. This miniaturization facilitates bunching of many electrodes in the smallest space.

The small disc consisting of the polymer may overhang the outer surface of the platinum wire in order to increase the contact area with the measuring liquid.

Thanks to the small area necessary several electrodes coated with various selective substances may be housed together in a very small space next to one another in a common measuring chamber, so that several ion activities may be determined in a single operation.

The new electrode is suited, because of its small dimensions, particularly for construction as a catheter electrode or for attachment to areas of a very few millimeters, e.g. in a living body.

Furthermore, the new electrode is suited, because of its small dimensions, particularly well to construction of a so-called single-rod measuring cell i.e. construction of an electrochemical cell in which the measuring electrode and the reference electrode are housed close to one another. These single-rod measuring cells are particularly suitable for flow measurement. Of course, here there is the difficulty that the known reference electrodes need a considerable amount of space in comparison to the new measuring electrode so that the miniaturization being striven for is in this respect hindered.

In fact, reference electrodes having a capillary contact area with the measuring liquid are known; however, in practice these have not given satisfactory results because they show unstable diffusion potentials. Therefore, in the professional world only those reference electrodes are recommended in which the contact making electrolyte providing the current path to the connection wire may pass into the measuring liquid through a non-lubricated ground connection (see the said book by Cammann, page 47). Therefore, it must be taken into account that the outflow rate of the contact making electrolyte is relatively large and therefore makes the measuring solution dirty and even poisons it. Furthermore, the contact making electrolyte must be supplied continuously.

Accordingly, therefore, in a specific embodiment of the invention, it is desired to re-shape the known reference electrodes so that a stable diffusion potential is achieved despite a very small contact area.

It was found that this may be achieved if the contact area consists of a microbore in a small plate made of polytetrafluoroethylene (PTFE).

The microbore may, for example, be formed so that a micronotch is arranged on the side wall of a stopper made of PTFE and that then this stopper is pressed into a corresponding opening in an electrode body consisting of PTFE. Another solution consists in welding a membrane made of PTFE on to the electrode body, the membrane being provided with a fine hole, for example by means of a laser beam. The microleak thus formed is so small that the outflow rate of the reference solution is less than $2.6 \times 10^{-6}$ $\mu$l/sec in normal pressure conditions. This construction of the contact area has proved to be rarely faulty as against previous experiences in the professional world, so that the reference potential could be successfully produced even with longer use.

The contact area, formed by the outlet opening, of the reference electrode thus manufactured may lie at a distance of less than 1 mm from the measuring electrode so that an extremely compact arrangement of a single-rod measuring cell may be created.

Use of the described reference electrode is, however, not limited to use together with the new measuring electrode, but may take place to advantage with conventional single and multi-rod measuring cells.

Single-rod measuring cells are in fact preferably used for flow measurement but are also advantageous for stationary measurements. This is valid all the more for single-rod measuring cells with multi-electrodes. In flow measurement, particularly in the physiological and pathophysiological region, it is frequently necessary to work with very low amounts of electrolyte. Thus it is desired, in preferred forms of the invention, to develop a single-rod measuring cell with the measuring and reference electrodes described above which may be put into use with simple means both for flow measurement and for stationary measurement and in which it is ensured that a measuring solution available only in small amounts comes into intimate contact with the contact zones of the electrodes.

For this purpose, according to an embodiment of the invention a bowl-shaped flow chamber is constructed in the region of the contact areas of the electrode body surrounded by the casing at the inner wall of the floor of a removable casing and the flow chamber is accessible via radial channels from the outer wall of the casing. If, therefore, the casing is removed, the single-rod measuring cell may be plunged into a beaker or the like with the measuring solution. If, on the other hand, the casing is pushed over the electrode body and is fixed for example by means of a retaining nut or a bayonet catch, then the edges of the bowl-shaped flow chamber seal against the outer surfaces of the electrode body and the measuring liquid may be supplied and removed through the channels, wherein said fluid comes into intimate contact with the entire measurement area thanks to the flattening of the flow chamber.

Referring now to the drawings, the main members of the shown measuring chain are an electrode head 1 with holes for an electrode plug 2 and a supply pipe 3 for the reference electrolyte, a casing 4, which is fixed to the electrode head 1 by means of a retaining nut 5 with a screwthread or a bayonet catch, and an electrode body 6 (FIG. 2) located in the casing. In the base member of the casing 4 are located pipe attachments 7 and 8, which act to supply and remove the measuring liquid.

The electrode head 1 and the retaining nut 5 comprise for example, polyacryl or metal, the casing 4 is made of polyacryl and the electrode body 6 is made of PTFE.

Figure 2:
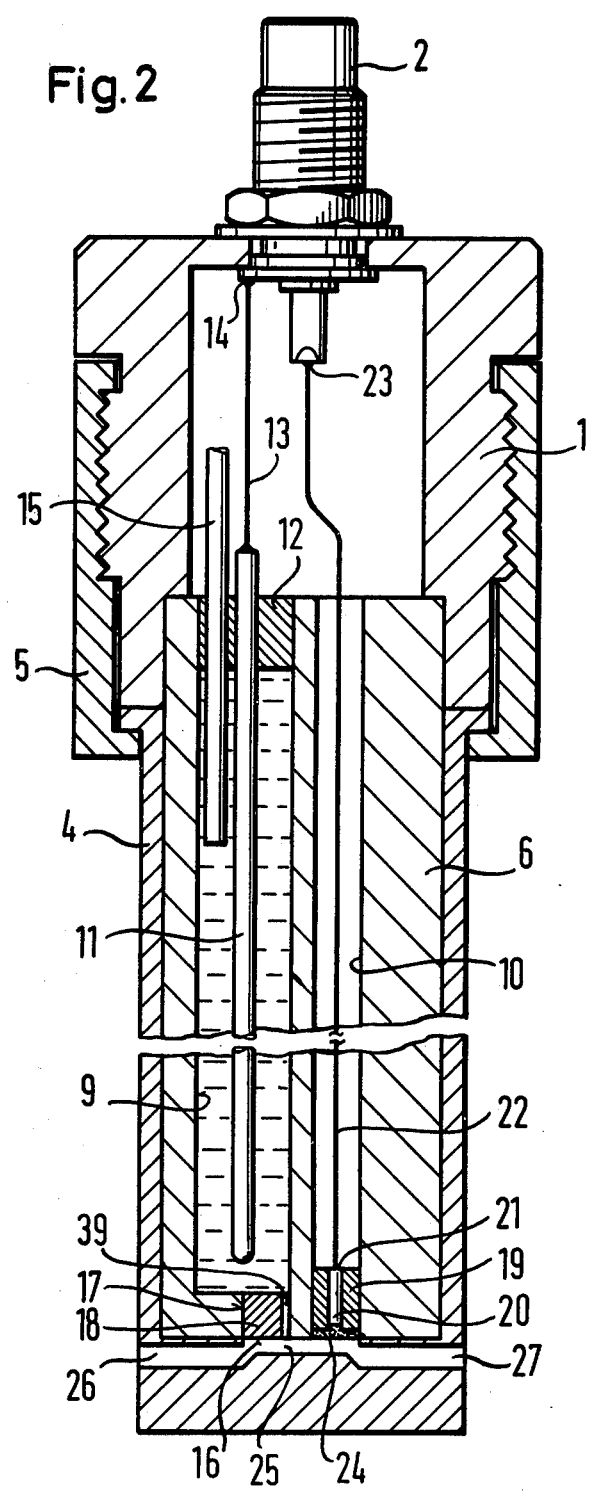
FIG. 2 shows a longitudinal section of the same.

As may be seen from FIG. 2, the electrode body 6 has two cylindrical longitudinal bores 9 and 10. The bore 9 acts to accommodate the reference electrode 11 made of Ag/AgCl, which passes through a stopper 12 at the upper end of the electrode body and is connected by means of a connecting wire 13 to the earth connection 14 of the coaxial plug 2. The stopper 12 is also penetrated by the end 15 of the delivery pipe 3 through which the contact making electrolyte (usually KCl) of the reference electrode may be supplied.

In the embodiment shown in FIG. 2, the bore 9 does not quite extend at its full width to the lower surface 16 of the electrode body 6, but is continued in a narrower aperture 17. This aperture 17 is closed by a stopper 18 made of PTFE which is pressed in and which is provided at one point on its circumference with a small longitudinal notch 39 the depth of which is not more than 0.1 mm, preferably less than 0.05 mm. The notch has such a flow resistance that the outflow rate of the reference solution is not more than about $5 \times 10^{-5}$ $\mu$l/sec under normal (atmospheric) pressure conditions, and is preferably less than $2.6 \times 10^{-6}$ $\mu$l/sec.

The longitudinal bore 10 has a low unobstructed width (e.g. 2 mm), as it does not have to accommodate any liquid. On its lower end there is located a stopper 19 made of polyacryl which has been bored through, in the longitudinal bore of which is inserted a platinum wire 20. A connecting wire 22 is soldered on to the inner face 21 of the platinum wire, said wire 22 leading to the inner lead 23 of the connecting plug 2.

The stopper 19 does not quite reach to the face 16 of the electrode body 6, but is set back from this by about 0.1 to 1 mm. The platinum wire 20 is also set back by a further small distance from the lower face of the stopper 19. A solid ion selective substance 24 is located in the bowl-shaped depression thus formed. It consists peferably of a polymer matrix (e.g. PVC) in which the active phase is incorporated. Thus, for example, a solution of PVC in cyclohexanone is mixed in a suitable ratio (15%) with the active phase which is selective for the desired ions and the mixture is poured into the bowl-shaped depression and dried.

An intimate contact of the selective substance with the wire is assured by the small distance that the platinum wire is set back and the danger of a direct contact of the wire with traces of leakage of the measuring liquid is reduced. Instead of platinum, another material having low potential drift may be used for the wire 20.

The face 16 of the electrode body 6 forms one limit of a flow chamber 25 constructed in the base of the casing 4. It has the shape of a flat bowl which is about 0.6 mm deep, the length and width of which are chosen so that the contact areas of the measuring electrode and the reference electrode lie completely in the measuring chamber. If, as in the present example the distance of the two contact areas is about 1 mm and the diameter of the contact area of the measuring electrode is about 2 mm, the width of the measuring chamber may also be 2 mm and its length 5 mm.

Radial channels 26 and 27 open in the centre of the narrow sides of the measuring chamber 25, which are bored from outside so far into the casing closely below the inner wall of the casing floor that the measuring chamber 25 is just cut. Attached to the channels 26 and 27 are the outer supply and removal pipes 7 and 8. Preferably the measuring liquid is supplied via the channel 27 and removed via the channel 26, so that first the measuring liquid comes into contact with the measuring electrode, and then with the reference electrode, so that any influencing of the result of measurement by the reference electrolyte may be avoided.

The cross-section of the measuring chamber 25 is approximately the same as that of the channels 26 and 27 so that the measuring liquid passes through at an even speed yet comes into abundant contact with the entire contact area as a result of the flat construction of the measuring chamber.

Figure 3:
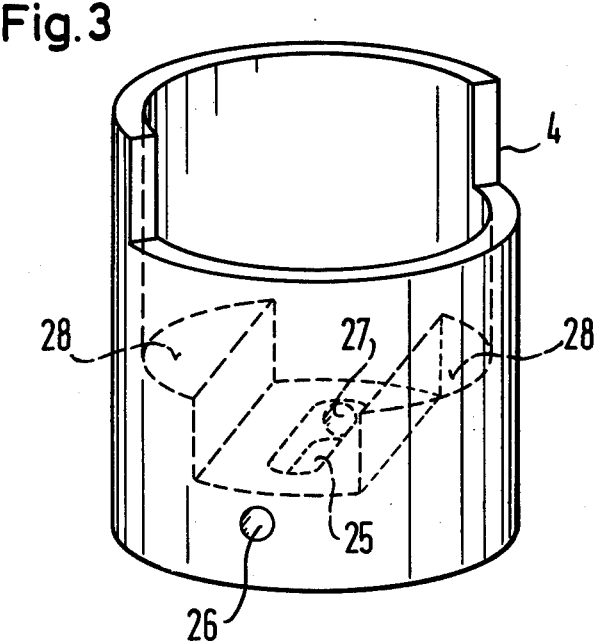
FIG. 3 shows a phantom diagram of the removable casing.

In order to ensure that the casing is correctly pushed over the electrode body, so that the edges of the measuring chamber seal both electrodes, the floor of the casing 4 is provided with projections 28 (FIG. 3) on both sides of the measuring chamber, these projections fitting into corresponding recesses 29 (FIG. 4) in the electrode body.

Figure 4:
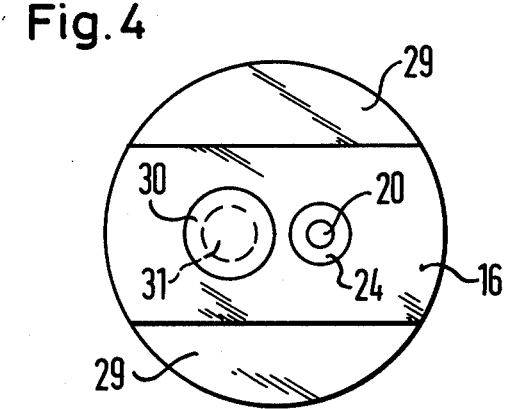
FIG. 4 shows a bottom view of a modified embodiment of the measuring cell with the casing removed.

FIG. 4 shows yet another modification of the embodiment of the reference electrode: instead of the stopper 18, here a thin membrane 30 made of PTFE is welded on to the face 16 of the electrode body in order to cover the opening 17. In the membrane 30 there is a small aperture 31 of approximately 0.01 mm $\phi$ (diameter) at the most, formed mechanically or electronically. This aperture size makes it possible to keep to the above-stated outflow speed also in this embodiment.

The described measuring chamber construction has proved to be insensitive to oscillations in the flow speed so that the measuring cell may be operated pulsatingly even with a simple pipe roller pump.

EXAMPLE

The calcium salt of didecyl phosphoric acid in dioctyl phenyl phosphonate was chosen as an active substance. The active phase was mixed in the above-described manner with PVC and the mixture was inserted into the bowl-shaped depression of the measuring electrode. After drying, the Ag/AgCl reference electrode was filled with 3-molar KCl solution and the casing was placed on top. Thus a calcium selective single-rod measuring cell is obtained.

The measuring chamber was connected to a liquid supply so that the measuring material at first passes the measuring electrode. A commercially common pipe roller pump was used as the pump.

First of all, the activity potential was determined in pure $CaCl_2$ solutions by measuring with different concentrations. The theoretical measurement characteristic of the electrodes (Nernst-factor) for di-valent ions is 29.083 mV/activity decade at 20° C. with the described flow metering chamber, a potential difference of 28.0 mV was measured between $10^{-2}$ and $10^{-3}$ mol $CaCl_2/l$.

The speed of indication is approximately 30 sec/activity decade in pure $10^{-2}$ and $10^{-3}$ mole solutions. In these conditions a measurement accuracy of ±0.4 mV and better could be achieved.

The selectivity was determined according to the principle of changing the measured ion activity when the activity of interfering ions is maintained constant. Aqueous solutions of $10^{-2}$ and $10^{-3}$ mole $CaCl_2/l$ were added as a chloride to the concentrations of interfering ions of 150 mval Na/l or 150 mval K/l or 150 mval Mg/l. Taking into account the non-ideal relationship of the solutions used, the following selectivity constants were ascertained from the measured potential changes:

$$K_{Ca-Na}=9.5\times10^{-3},\ K_{Ca-K}=3\times10^{-4},$$
$$K_{Ca-Mg}=1.8\times10^{-3}.$$

In contrast, in the literature on the subject (see Cammann, page 98) the following values are found for liquid membrane electrodes with the same active phase:

$$K_{Ca-Na}=10^{-3},\ K_{Ca-K}=10^{-3},\ K_{Ca-Mg}=14\times10^{-3}.$$

The measurements of the potential were carried out with the digital pH meter E 500 by the Metrohm company (Herisau, Switzerland).

The described electrode and also the measuring cell constructed therewith are particularly suitable as one-time and disposable electrodes because of their simplicity and relatively cheap manufacture.

It will be understood that the above description of the present invention is susceptible to various modification changes and adaptations.

What is claimed is:

1. A reference electrode for use with an ion selective electrode comprising:
   (a) an electrode body made of polytetrafluoroethylene, said body including a chamber for an electrolyte solution; and
   (b) a stopper, said stopper being pressed into said electrode body and having a micro notch in the side wall thereof to provide a single aperture in the body as the sole electroytic communicating means between said chamber and the outside of said body, said aperture being of a size to restrict flow of electrolyte therethrough at normal pressure and room temperature to a rate of less than $5\times10^{-6}$ micro liters per second.

2. A reference electrode in accordance with claim 1 wherein the rate of flow of the electrolyte is less than $2.6\times10^{-6}$ micro liters per second.

3. An electrode in accordance with claim 1 wherein the depth of said micro notch is less than 0.1 millimeters.

4. An electrode in accordance with claim 1 wherein the depth of said micro notch is less than 0.05 millimeters.

5. A reference electrode for use with an ion selective electrode comprising:
   (a) an electrode body made of polytetrafluoroethylene, said body including a chamber for an electrolyte solution and having an opening therein;
   (b) a polytetrafluoroethylene plate sealed over said opening to close the same,
   (c) a single aperture in said plate of sufficiently small diameter to restrict the flow of the electrolyte therethrough to a rate of less than $5\times10^{-6}$ micro liters per second as the sole electrolytic communicating means between the body and the outside of the body.

6. An electrode in accordance with claim 5 wherein said aperture has a diameter of less than 0.01 millimeters.